United States Patent
Breliere et al.

(10) Patent No.: US 6,235,791 B1
(45) Date of Patent: May 22, 2001

(54) USE OF AMINES TO PRODUCE DRUGS FOR PREVENTING TUMOR CELL PROLIFERATION

(75) Inventors: Jean Claude Breliere, Montpellier; Pascual Ferrara, Avignonet Lauragais; Christine Lebouteiller, Pechabou; Raymond Paul, Saint Gely du Fesc; Jorge Rosenfeld, Baziege; Didier Van Broeck, Murviel lés Montpellier, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/230,643
(22) PCT Filed: Jul. 28, 1997
(86) PCT No.: PCT/FR97/01409
  § 371 Date: Apr. 12, 1999
  § 102(e) Date: Apr. 12, 1999
(87) PCT Pub. No.: WO98/04251
  PCT Pub. Date: Feb. 5, 1998

(30) Foreign Application Priority Data

Jul. 29, 1996 (FR) .................................................. 96 09531

(51) Int. Cl.$^7$ ........................ A61K 31/135; C07C 211/39
(52) U.S. Cl. ...................... 514/650; 514/212; 514/227.5; 514/239.5; 514/255; 514/317; 514/422; 514/425; 514/461; 514/617; 514/654; 564/161; 564/337; 564/342; 564/345
(58) Field of Search ................................ 514/212, 227.5, 514/239.5, 255, 317, 422, 425, 461, 617, 650, 654; 540/484, 609, 610, 612; 544/59, 106, 178, 403, 578; 546/16, 192; 548/465, 548, 578; 549/102; 564/161, 337, 342, 345

(56) References Cited

U.S. PATENT DOCUMENTS

| 3,674,832 | 7/1972 | Sherlock et al. ...................... 560/102 |
| 4,104,383 | 8/1978 | Krausz ............................... 514/239.5 |
| 4,537,902 | 8/1985 | Cragoe, Jr. et al. ................. 514/422 |
| 5,230,092 | 7/1993 | Lavastre et al. . |
| 5,354,781 | 10/1994 | Breliere et al. ....................... 514/650 |
| 5,919,934 | * 7/1999 | John ..................................... 546/247 |

FOREIGN PATENT DOCUMENTS

| 376850 | * 7/1990 | (EP) . |
| 461986 | * 12/1991 | (EP) . |
| 581677 | * 2/1994 | (EP) . |
| 702010 | * 3/1996 | (EP) . |
| 707004 | * 4/1996 | (EP) . |
| 2132547 | 7/1974 | (FR) . |
| 2 050 358 | 1/1981 | (GB) . |
| 95/15948 | * 7/1995 | (WO) . |
| 95/8532 | 10/1995 | (ZA) . |

OTHER PUBLICATIONS

S. Silve et al., *Molecular and Cellular Biology*, Jun. 1996, p. 2719–2727.
P. Casellas et al., *Journal of Neuroimmunology*, 52 (1994), pp. 193–203.
B. Vilner, B. De Costa and W. Bowen, *Journal of Neuroscience*, Jan. 1995, 15(1), pp. 117–134.
P. Brent and G. Pang, *European Journal of Pharmacology*, 278 (1995), pp. 151–160.
B. Bourrié et al., *Immunology*, 88 (1996), pp. 389–393.
Webster Third New international dictionary, p. 1814, 1988.*
Su et al. "Sigma compounds derived from . . . " Derwent Accession No. 92–08787, 1992.*
Burdman et al. "Control of cell proliferation and . . . " CA 94:114534, 1980.*
Su et al. "Correlation of inhibitory potencies . . . " Ca 108:216255, 1988.*
Glennon et al. "Novel 1–phenylpiperazine . . . " CA 116:6512, 1991.*
Paul et al. "Allosteric modulation of peripheral . . . " CA 121:271560, 1994.*
Laroque et al. "Quantitative evaluation of . . . " CA 124:552, 1995.*
Kleeb et al. "Effect of haloperidol on the . . . " CA 126:84184, 1996.*

* cited by examiner

Primary Examiner—Ceila Chang
(74) Attorney, Agent, or Firm—Michael D. Alexander

(57) ABSTRACT

The present invention relates to the use of compounds capable of displacing tritiated cis-N-cyclohexyl-N-ethyl [3-(3-chloro-4-cyclohexylphenyl)-allyl]amine from its receptors for the preparation of pharmaceutical compositions intended to combat cell proliferation.

3 Claims, 2 Drawing Sheets

USE OF AMINES TO PRODUCE DRUGS FOR PREVENTING TUMOR CELL PROLIFERATION

This application is a 371 of PCT/FR97/01409 filed Jul. 28, 1997.

The present invention relates to a novel use of compounds having good affinity for the receptors to which cis-N-cyclohexyl-N-ethyl [3-(3-chloro-4-cyclohexylphenyl) allyl]amine binds, as well as to novel compounds having the same properties.

cis-N-Cyclohexyl-N-ethyl [3-(3-chloro-4-cyclohexylphenyl)allyl]amine, also known under the code CM 31747 or SR 31747 and referred to hereinbelow as "SR 31747", is described in EP 376,850 which also discusses its immunosuppressant activity. It has been found that SR 31747 prevents cancer cells from proliferating and that, consequently, it can exert antitumour activity.

Furthermore, it has been found that SR 31747 has receptor sites on these cells.

Lastly, it has been found that any product capable of displacing tritiated SR 31747 from its receptors on tumour cells prevents cell proliferation. More particularly, it has been observed that compounds capable of displacing tritiated SR 31747 (referred to hereinbelow as "$^3$H-SR 31747") from its receptor sites have activity in preventing cell proliferation.

Thus, according to one of its aspects, the present invention relates to the use of compounds capable of displacing tritiated cis-N-cyclohexyl-N-ethyl [3-(3-chloro-4-cyclohexylphenyl)allyl]amine from its receptors for the preparation of pharmaceutical compositions intended to combat cell proliferation. The capacity of the compounds envisaged for the use according to the present invention of displacing tritiated SR 31747 from its receptors may readily be determined biochemically using $^3$H-SR 31747 and binding it to the cells.

This determination may be carried out with tumour cells chosen appropriately, preferably from cell lines which proliferate readily in vitro, for example human myeloma, kidney carcinoma or human lung cells or alternatively on mammary carcinoma cells.

In the context of the present invention, in order to be able to carry out the determinations under standardized conditions making it possible to obtain constant and reproducible results, a human mammary tumour cell line "MCF-7" was chosen arbitrarily.

Also, in the context of the present invention, $^3$H-SR 31747 was chosen arbitrarily, in which the tritium is bound to the vinylene bond, but the Sr 31747 may be labelled in any way at all since the labelling serves only to monitor the displacement of the product from its receptors.

Determination of the capacity to displace $^3$H-SR 31747 from its receptors present on cells, in particular cells of the MCF-7 cell line, was carried out by performing tests of total binding and of specific binding.

According to the present invention, any product which, when subjected to the above preliminary operation, is capable of displacing $^3$H-SR 31747 from its receptors may be used for the preparation of pharmaceutical compositions to combat cell proliferation. SR 31747 is, firstly, capable of displacing $^3$H-SR 31747 from its receptors and possesses powerful inhibitory activity on cell proliferation. More particularly, the subject of the present invention is the use of a compound capable of displacing tritiated cis-N-cyclohexyl-N-ethyl[3-(3-chloro-4-cyclohexylphenyl)allyl] amine from its receptors, chosen from the group consisting of:

a) amines of formula

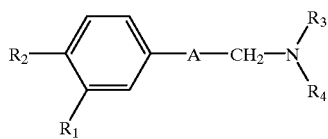

(I)

in which $R_1$ represents a hydrogen atom or a halogen atom;

$R_2$ represents a cyclohexyl;

$R_3$ represents a cycloalkyl containing from 3 to 6 carbon atoms;

$R_4$ represents a hydrogen atom, an alkyl containing from 1 to 6 carbon atoms or a cycloalkyl containing from 3 to 6 carbon atoms;

A represents a group chosen from: —CO—CH$_1$—, —CH(Cl)—CH$_2$—, —CH(OH)—CH$_2$, —CH$_2$, —CH=CH—, —C≡C—;

b) pharmaceutically acceptable addition salts of the amines of formula (I);

c) amines of formula (II)

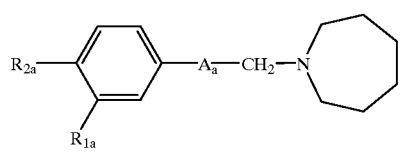

(II)

in which $A_a$ is a group chosen from the following: —CO—CH$_2$—; —CH(OH)—CH$_2$; —CH=CH—; —C≡C—;

$R_{1a}$ represents hydrogen or a halogen;

Rphd 2ais a cyclohexyl group;

d) the addition salts of a pharmaceutically acceptable acid of the amines of formula (II);

e) amines of formula (III)

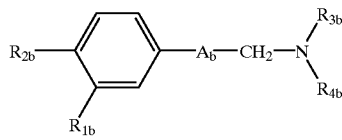

(III)

in which;

$R_{1b}$ represents a hydrogen atom or a halogen atom;

$R_{2b}$ represents a cyclohexyl group;

$R_{3b}$ represents a hydrogen atom or a $C_1$–$C_3$ alkyl group;

$R_{4b}$ represents a $C_1$–$C_3$ alkyl group which may be identical $R_{3b}$ and $R_{4b}$ considered together may form, with the nitrogen atom to which they are attached, a 5- to 7-membered heterocyclic group chosen from piperidino, morpholino and pyrrolidino;

$A_b$ represents a —CH$_2$CH$_2$— or —CH=CH— group;

f) the pharmaceutically acceptable addition salts with acids of the amines of formula (III).

g) amines of formula (IV)

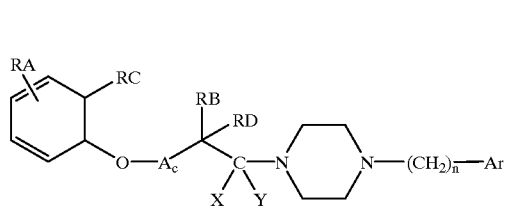

(IV)

in which $A_{c1}$ represents a phenyl, naphthyl, substituted phenyl or substituted naphthyl group, n represents an integer between 1 and 4 inclusive, RB represents an alkyl group and, in this case, $A_c$ represents a single bond and RA and RC, which may be identical or different, represent, independently of each other, a hydrogen atom or a group chosen from halogen, alkyl, alkyl substituted with one or more halogens, and alkoxy, or RB and RC together form a bridge —(CH$_2$) p- with p representing 0, 1 or 2 and, in this case, RA represents a hydroxyl or alkoxy group in position 5 on the aromatic ring which bears it or RA represents a hydrogen or halogen atom in any position on the aromatic ring, or RB and RC together form a —CH= bridge, and the bond with links it to the aromatic ring is a single bond and, in this case, $A_c$ represents a CH$_2$ group and RA represents a hydrogen atom or a hydroxyl or alkoxy group in position 5 on the aromatic ring which bears it, or RB and RC together form a bond and $A_c$ then represents a group

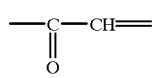

the carbonyl being linked to the oxygen and the bond connecting $A_c$ to the carbon bearing the side chain is a double bond, and, in this case, RA represents a hydrogen atom or a hydroxyl or alkoxy group, when RB represents an alkyl group, X and Y each represent two hydrogen atoms or form, together with the carbon atom which bears them, a C=O group, and RD represents a hydrogen atom or an alkyl group, when RB and RC form a bridge, X and Y each representing two hydrogen atoms and RD, which exists only when all the bonds of the carbon which bears it are single bonds, represents a hydrogen atom, it being understood that the terms "alkyl" and "alkoxy" denote linear or branched saturated groups containing from 1 to 6 carbon atoms.

the term "substituted" relating to the phenyl and naphthyl substituents means that these may be substituted with 1 to 3 groups chosen from hydroxyl, alkyl, alkyl substituted with one or more halogens, alkoxy and halogen, the pharmaceutically acceptable salts and solvates of the amines of formula (IV);

i) amines of formula (V)

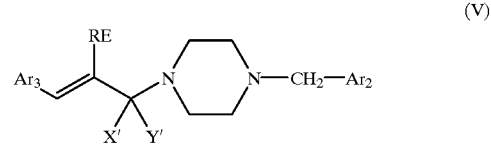

(V)

in which:

$A_{r2}$ and $A_{r3}$, which may be identical or different, represent, independently of each other, a phenyl group, or a naphthyl or phenyl group substituted with 1 to 3 groups chosen from hydroxyl, (C$_1$–C$_6$) alkyl, alkoxy, halogen and alkyl, and alkyl substituted with one or more halogens;

X' and Y' each represent two hydrogen atoms or together form an oxo group,

RE represents a (C$_1$–C$_6$) alkyl group, their isomers in pure form or in the form of a mixture.

j) the pharmaceutically acceptable salts and solvates of the amines of formula (V)

k) amines of formula (VI)

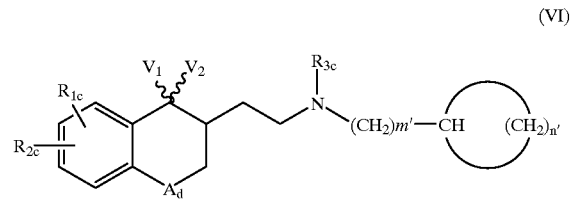

(VI)

in which:

$R_{3c}$ is H or (C$_1$–C$_3$) alkyl;

$R_{1c}$ and $R_{1c}$, which may be identical or different, are chosen from H, OH, (C$_1$–C$_3$) alkyl, (C$_1$–C$_3$) alkoxy, halogen and cyano; $V_1$ and $V_2$ together form a double bond linked to an oxygen atom or alternatively a hydroxyimino radical N—OH, or alternatively are connected as an ethylenedioxy chain —O—CH$_2$—CH$_2$—O—;

$A_d$ represents a valency bond, an oxygen atom, a methylene group or an ethylene group; m' is equal to zero, 1 or 2;

n' is an integer from 1 to 5;

l) the pharmaceutically acceptable addition salts with acids of the amines of formula (VI)

m) amines of formula (VII)

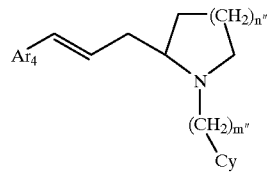

(VII)

in which m" and n" represent 1 or 2,

Cy represents a (C$_3$–C$_7$) cycloalkyl,

Ar$_4$ represents an aryl or a heteroaryl chosen from phenyl, naphthyl and thienyl, optionally mono- to tri- substituted with a halogen, a trifluoromethyl, a $(C_1-C_3)$ alkyl or a $(C_1-C_3)$ alkoxy;
n) the pharmaceutically acceptable addition salts with acids of the amines of formula (VII),
o) amines of formula (VIII)

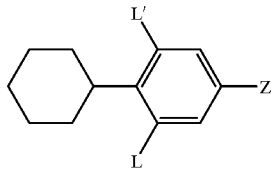

(VIII)

in which:
one of the groups L and L' is hydrogen and the other is chosen from hydrogen, fluorine, chlorine and nitro or alternatively L and L' are both chlorine atoms,
Z represents
(i) a group of structure

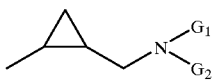

(1)

in which
$G_1$ represents a $(C_1-C_6)$ alkyl or a $(C_3-C_7)$ cycloalkyl,
$G_2$ represents a $(C_1-C_6)$ alkyl, a $(C_3-C_6)$ cyclo-alkyl $(C_1-C_3)$ alkyl, a $(C_3-C_7)$ cycloalkyl, a phenyl, benzyl or phenethyl group optionally substituted on the phenyl nucleus of the radical with a halogen or with a methoxy or nitro group,
or alternatively $G_1$ and $G_2$ form, together with the nitrogen atom to which they are attached, a saturated, bridged or spiro heterocycle having only one endocyclic nitrogen atom and containing from 5 to 10 carbon atoms; a morpholino group; a piperazino group which is unsubstituted or substituted in position 4 with a $(C_1-C_4)$ alkyl, with a phenyl, benzyl or phenethyl radical, the benzene group optionally being substituted with a halogen, or with a methoxy or nitro group; a group chosen from 4-phenyl-1,2,3,6-tetrahydropyrid-1-yl, 4-phenylpiperidino, 4-benzylpiperidino and 4-phenethylpiperidino radicals, it being possible for the phenyl group of the said radicals to be unsubstituted or substituted with a halogen or with a methoxy group or a nitro group,
(ii) a group of structure (2)

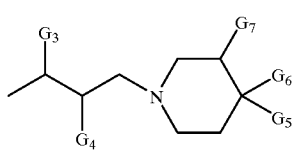

(2)

in which
$G_3$ represents hydrogen or a hydroxyl group;
$G_4$ represents hydrogen;
or alternatively $G_3$ and $G_4$ together constitute one or two bonds so as to form, with the carbon atoms to which they are attached, a vinylene group or ethynylene group;

$G_5$ represents a group chosen from phenyl, benzyl and phenethyl radicals, it being possible for the phenyl nucleus of the said radicals to be unsubstituted or substituted with a halogen, a methoxy group or a nitro group;
$G_6$ represents a hydroxyl group or a hydrogen;
$G_6$ and $G_7$ represent hydrogen or may form a bond;
or alternatively $G_5$ and $G_5$ and $G_6$ together form an n-pentylene group;
(iii) a group of structure (3)

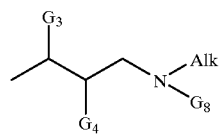

(3)

in which
$G_3$ and $G_4$ are as defined above;
Alk represents a $(C_1-C_6)$ alkyl or a $(C_3-C_6)$ alkenyl;
$G_8$ represents a 1-adamantyl, a $(C_3-C_7)$ cycloalkyl, a $(C_3-C_7)$ cycloalkyl $(C_1-C_3)$ alkyl or a group chosen from phenyl, benzyl and 2-phenethyl radicals, it being possible for the phenyl nucleus of the said radicals to be unsubstituted or substituted with a halogen, methoxy group or a nitro group,
or alternatively Alk and $G_3$, which may be identical or different, represent a $(C_4-C_6)$ alkyl group;
$G_3$ not being a $(C_3-C_6)$ cycloalkyl when L is hydrogen or a fluorine or chlorine atom, L' is hydrogen and Alk is a $(C_1-C_6)$ alkyl;
p) the pharmaceutically acceptable salts and solvates of the amines of formula (VIII).

The compounds whose use is claimed in the present invention are partly described in the literature.

In particular, the amines of formula (I) and their pharmaceutically acceptable salts are described in EP 376,850; the said amines may be prepared as illustrated in that document and isolated in the form of base, salts and/or solvates. The amines of formula (II) and their pharmaceutically acceptable salts are described in EP 461,986; the said amines may be prepared as illustrated in that document and isolated in the form of base, salts and/or solvates. The amines of formula (III) and their pharmaceutically acceptable salts are described in FR 2,249,659; the said amines may be prepared as illustrated in that document and isolated in the form of base, salts and/or solvates. The amines of formula (IV) and their pharmaceutically acceptable salts are described in EP 702,010; the said amines may be prepared as illustrated in that document and isolated in the form of base, salts and/or solvates. The amines of formula (V) and their pharmaceutically acceptable salts are described in EP 707,004; the said the amines may be prepared as illustrated in that document and isolated in the form of base, salts and/or solvates. The amines of formula (VI) and their pharmaceutically acceptable salts are described in EP 581,677; the said amines may be prepared as illustrated in that document and isolated in the form of base, salts and/or solvates. The amines of formula (VII) and their pharmaceutically acceptable salts are described in WO 95/15948; the said amines may be prepared as illustrated in that document and isolated in the form of base, salts and/or solvates.

The compounds of groups (o) and (p), which are particularly advantageous, are novel and constitute a further aspect of the invention.

Thus, the invention also relates to novel compounds which displace $^3$H SR 31747 from its receptors in the same way and which possess noteworthy antiproliferative properties, and the pharmaceutical compositions which contain them. More particularly, the subject of the invention is also an amine chosen from:

(A) a compound of formula

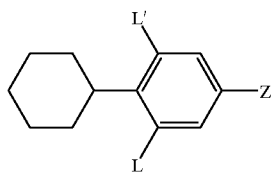

(VIII)

in which:

one of the groups L and L' is hydrogen and the other is chosen from hydrogen, fluorine, chlorine and nitro or alternatively L and L' are both chlorine atoms, Z represents (i) a group of structure

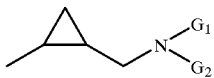

(1)

in which $G_1$ represents a $(C_1-C_6)$ alkyl or a $(C_3-C_7)$ cycloalkyl, $G_2$ represents a $(C_1-C_6)$ alkyl, a $(C_3-C_6)$ cycloal-kyl $(C_1-C_3)$ alkyl, a $(C_3-C_7)$ cycloalkyl, a phenyl, benzyl or phenethyl group optionally substituted on the phenyl nucleus of the radical with a halogen or with a methoxy or nitro group, or alternatively $G_1$ and $G_2$ form, together with the nitrogen atom to which they are attached, a saturated, bridged or spiro heterocycle having only one endocyclic nitrogen atom and containing from 5 to 10 carbon atoms; a morpholino group; a piperazino group which is unsubstituted or substituted in position 4 with a $(C_1-C_4)$, with a phenyl, benzyl or phenethyl radical, the phenyl nucleus optionally being substituted with a halogen, or with a methoxy or nitro group; a group chosen from 4-phenyl-1,2,3,6-tetrahydropyrid-1-yl, 4-phenylpiperidino, 4-benzyl-piperidino and 4-phenethylpiperidino radicals, it being possible for the phenyl group of the said radicals to be unsubstituted or substituted with a halogen or with a methoxy group or a nitro group, (ii) a group of structure (2)

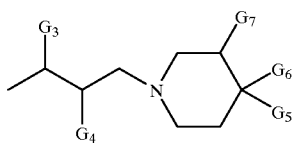

(2)

in which $G_3$ represents hydrogen or a hydroxyl group;

$G_4$ represents hydrogen;

or alternatively $G_3$ and $G_4$ together constitute one or two bonds so as to form, with the carbon atoms to which they are attached, a vinylene group or an ehtynylene group;

$G_5$ represents a group chosen from phenyl, benzyl and phenethyl radicals, it being possible for the phenyl nucleus of the said radicals to be unsubstituted or substituted with a halogen, methoxy group or a nitro group;

$G_6$ represents a hydroxyl group or a hydrogen;

$G_6$ represent hydrogen or may form a bond;

or alternatively $G_5$ and $G_6$ together form an n-pentylene group;

$G_6$ being a hydroxyl group and it being possible for $G_5$ and $G_7$ to form a bond only when $G_5$ is other than optionally substituted benzyl or phenethyl, (iii) a group of structure (3)

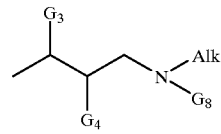

(3)

in which $G_3$ and $G_4$ are as defined above;

Alk represents a $(C_1-C_6)$ alkyl or a $(C_3-C_4)$ alkenyl;

$G_a$ represents a 1-adamantyl, a $(C_3-C_7)$ cycloalkyl, a $(C_3-C_7)$ cycloalkyl $(C_1-C_3)$ alkyl or a group chosen from phenyl, benzyl and 2-phenylethyl radicals, it being possible for the phenyl nucleus of the said radicals to be unsubstituted or substituted with a halogen, a methoxy group or a nitro group, or alternatively Alk and $G_8$, which may be identical or different, represent a $(C_4-C_6)$ alkyl group;

$G_8$ not being a $(C_3-C_6)$ cycloalkyl when L is hydrogen or a fluorine or chlorine atom, L' is hydrogen and Alk is a $(C_1-C_6)$ alkyl;

(B) the pharmaceutically acceptable salts and solvates of the compound of formula (VIII).

In these novel compounds of formula (VIII), the halogen is preferably chlorine or fluorine, one of the groups L and L' being hydrogen and the other fluorine, chlorine or nitro or alternatively L and L', which are identical, being hydrogen or chlorine. These compounds are particularly advantageous.

Among these particularly advantageous compounds, those in which, in formula (VIII), Z represents (i') a group of structure (1')

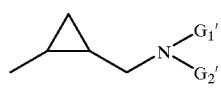

(1')

in which $G_1$ represents a $(C_1-C_6)$ alkyl or a $(C_3-C_7)$ cycloalkyl;

$G_2$ represents a $(C_1-C_6)$ alkyl, $(C_3-C_7)$ cycloalkyl $(C_1-C_3)$ alkyl, a $(C_3-C_7)$ cycloalkyl or a group chosen from phenyl, benzyl and 2-phenylethyl radicals, it being possible for the phenyl nucleus of the said radicals to be unsubstituted or substituted with a halogen or with a methoxy or nitro group, —or alternatively $G_1$ and $G_2$ form, together with the nitrogen atom to which they are attached, a morpholino, pyrrolidino, piperidino or hexahydroazepino group or a group chosen from 4-phenyl-1,2,3,6-tetrahydropyrid-1-yl, 4-pheynlpiperidino, 4-benzylpiperidino and 4-phenethylpiperidino radicals, it being possible for the phenyl group of the said radicals to be unsubstituted or substituted with a halogen or with a methoxy group or a nitro group, (ii') a group of structure (2')

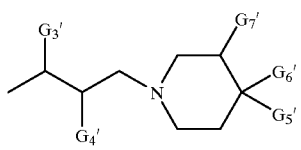

(2')

in which $G_3$ and $G_4$ are hydrogen or together form a bond, in that trans or, preferably, cis configuration, $G_3$ and $G_7$ are hydrogen and $G_5$ is phenyl or benzyl, or alternatively $G_5$ and $G_6$ together form a 1,5-pentylene group;

(iii') a group of structure (3')

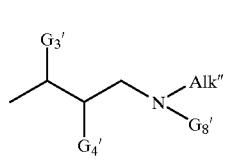

(3')

in which $G_3$ and $G_4$ are as defined above, Alk" is $(C_1-C_6)$ alkyl, $G_3$ represents a 1-adamantyl, phenyl, benzyl or 2-phenylethyl group or alternatively Alk" and $G_8$, which are identical, each represent a $(C_4-C_6)$ alkyl group, and their pharmaceutically acceptable salts and solvates, are preferred.

These novel compounds of formula (VIII) may be prepared by a process characterized in that:

either, a functional derivative of cyclopropane-carboxylic acid of formula (IX)

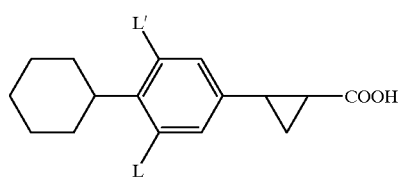

(IX)

in which L and L' are as defined above, is reacted with an amine of formula (X)

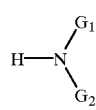

(X)

in which $G_1$ $G_2$ are as defined above, and the amide thus obtained of formula (XI)

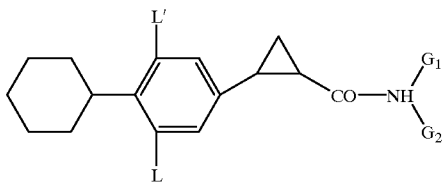

(XI)

is then subjected to reduction in order to isolate the amines of formula (VIII), in which Z is a group of structure (1), in the form of their free bases or their pharmaceutically acceptable salts;

or, a compound of formula (XII)

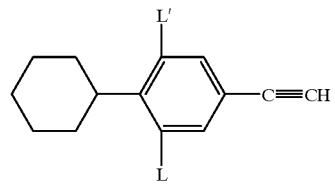

(XII)

in which L and L' are as defined above, is reacted with formaldehyde and an amine chosen from those of formulae (XIII) and (XIV)

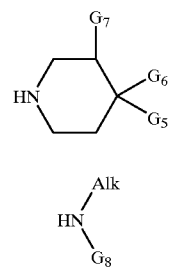

(XIII)

(XIV)

and the product thus obtained of formula (VIII) in which Z has the structure (2) or (3) where $G_3$ and $G_4$ together constitute two bonds so as to form, with the carbon atoms to which they are attached, an ethynylene group, is optionally subjected to hydrogenation with two or one mole of hydrogen so as to isolate the corresponding compound of formula (VIII) in which Z is a group of structure (2) or (3) where $G_3$ and $G_4$ both respectively represent a hydrogen atom or, together, a bond which forms, with the two carbon atoms to which they are attached, a vinylene group; or the product thus obtained of formula (VIII) in which Z has the structure (2) where $G_5$ is phenyl, $G_6$ is hydroxyl and $G_7$ is hydrogen, is optionally subjected to dehydration in order to isolate a compound of formula (VIII) in which Z has the structure (2) where $G_5$ is phenyl and $G_6$ and $G_7$ together form a bond; it being possible for the said compounds to be isolated in the form of their free base or one of their pharmaceutically acceptable salts or solvates;

or, an acetophenone of formula (XV)

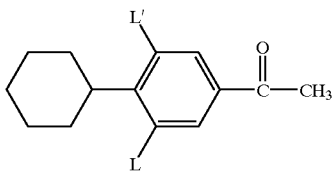

(XV)

in which L and L' are as defined above, is reacted with formaldehyde and an amine of formula (XIII) or (XIV) above, and the product thus obtained of formula (XVI)

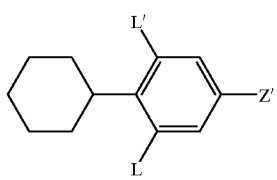

(XVI)

in which L and L' are as defined above and Z'0 represents a structure (2') or (3')

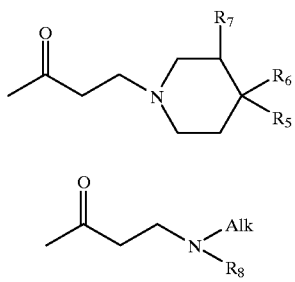

(2')

(3')

where Alk, $R_5$, $R_6$, $R_7$ and $R_8$ are as defined above, is then subjected to reduction of the ketone so as to isolate the corresponding compound of formula (VIII) in which Z is a group of structure (2) or (3) or $G_3$ is hydroxyl and $G_4$ is hydrogen, after which the product thus obtained of formula (VIII), in which Z has the structure (2) where $G_5$ is phenyl, $G_6$ is hydroxyl and $G_7$ is hydrogen, is optionally subjected to dehydration in order to isolate a compound of formula (VIII) in which Z has the structure (2) where $G_5$ is phenyl and $G_6$ and $G_7$ together form a bond; it being possible for the said compounds to be isolated in the form of their free base or one of their pharmaceutically acceptable salts; and the free bases of formula (VIII) are optionally converted into their pharmaceutically acceptable salts.

Reaction of the functional derivative of the acid (IX) with the amine (X) takes place according to the standard procedures for the preparation of amides. As a functional derivative of the acid (IX), any common compound of peptide chemistry may be used, for example the chloride, the anhydride, a mixed anhydride, for example with carbonic acid monoethyl ester (obtained by reacting the acid (IX) with ethyl chloroformate), an activated ester or an activated amide. When, as a functional derivative, the chloride or the anhydride is used, it may be advantageous to work in the presence of a tertiary amine, for example triethylamine.

The compound (XI) may also be reduced under the standard conditions for converting an amide into an amine, using a metal iodide such as lithium aluminum hydride or borane as reducing agent. The reaction between the acetylene derivatives (XII) or the acetophenones (XV) and the amines (XIII) and (XIV) in the presence of formaldehyde is carried out under the standard conditions of the Mannich reaction.

Reduction of the compounds of formula (VIII), in which Z has one of the structures (2) or (3) where $G_3$ and $G_4$ form two bonds, is carried out by hydrogenation with one mole of hydrogen in order to obtain the compounds (VIII) (Z=structure 2 or 3 where $G_3+G_4$ form a bond of cis configuration) or with two moles of hydrogen in order to obtain the saturated compounds.

Reduction of the compound of formula (XVI) in order to obtain the compounds of formula (VIII) in which Z has one of the structures (2) or (3) where $G_3$ is hydroxyl and $G_4$ is hydrogen, is carried out according to the standard methods. When it is desired to obtain a hydroxy compound having a specific configuration on the chiral carbon atom, a stereospecific reducing agent may be used.

When the hydroxylated derivative must then be dehydrated in order to obtain a compound of formula (VIII), in which Z has one of the structures (2) or (3) where $G_3$ and $G_4$ form a bond, the stereoconfiguration plays no role and the compound (XVI) may be reduced, for example, with sodium borohydride.

The optional dehydration of the compound of formula (VIII), in which Z has one of the structures (2) or (3) where $G_3$ is hydroxyl and $G_4$ is hydrogen, is carried out by heating in the presence of agents or apparatus which promote the removal and/or uptake of water, for example using Dean-Stark apparatus.

The configuration of the unsaturated compound (VIII) thus obtained is trans. This compound may in turn be hydrogenated in order to prepare an amine of formula (VIII) in which Z has one of the structures (2) or (3) where $G_3$ and $G_4$ are hydrogen.

The starting acids of formula (IX) and their functional derivatives, as well as the amides of formula (XI), are novel products which may be prepared from a 4-(4-cyclohexyl-3,5-L-L'-phenyl)-4-oxobutyric acid.

More particularly, the acids of formula (IX) are obtained by reduction of the ketone to 4-(4-cyclohexyl-3,5-L-L'-phenyl)-4-cyclohexyl-3,5-L-L'-phenyl)-4-hydroxybutyric acid which is converted into its lactone. This lactone is chlorinated and converted into 4-chloro-4-(4-cyclohexyl-3,5-L-L'-phenyl)butyric acid ester which in turn gives, on cyclization, the cyclopropanecarboxylic acid (IX).

The 4-(4-cyclohexyl-3,5-L-L'-phenyl)-4-oxo-butyric acids (L and L' being as defined above) are prepared in the following way:

when L and L' represent H, according to N. P. Buu-Hoï et al., Bull. Soc. Chim. France, 1944, 127;

when L represents H, L' represents Cl according to F. Krausz et al., Arzneim.-Forsh., 1974, 24, 1364–1367; BE 750,233;

when L represents H, L' represents $NO_2$ according to BE 750,233;

when L and L' represent Cl, according to F. Krausz et al., Arzneim-Forsch., 1974, 24, 1364_14 1367;

when L represents H, L' represents F by catalytic hydrogenation of 3-(4-cyclohexyl-3-fluoro)benzoyl-acrylic acid, which is itself described in JP 75770/71 and DE 2,103,749.

Thus, the acids of formula IX may be obtained by a process in which:

a 4-oxobutyric acid of formula

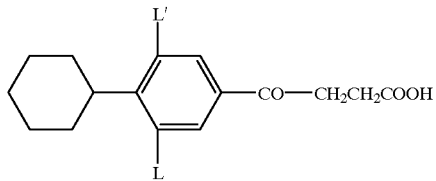
(XVII)

in which L and L' are as defined above, is reduced with an alkali metal borohydride;

the 4-hydroxybutyric acid thus obtained of formula

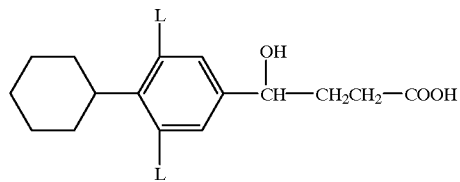
(XVIII)

is cyclized by heating while removing the water which forms the lactone thus obtained, of formula

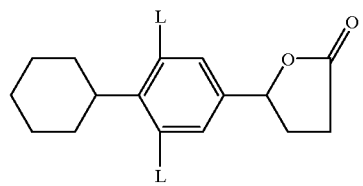
(XIX)

is treated with thionyl chloride, isolating, in a $(C_1–C_4)$ alkanol, an ester of formula

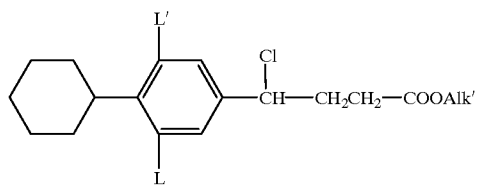
(XX)

in which Alk' is a $(C_1–C_4)$alkyl;

compound (XX) thus obtained is cyclized by heating in the presence of potassium t-butoxide and the cyclopropanecarboxylic acid of formula (IX) is isolated.

The acids of formula (IX), their salts, their functional derivatives, in particular the chloride, the anhydride and the mixed anhydride with a mono-$(C_1–C_4)$alkyl ester of carbonic acid, as well as the amides of formula (XI), are novel products which constitute a further aspect of the present invention.

Thus, the present invention also relates to a compound of formula (XXI)

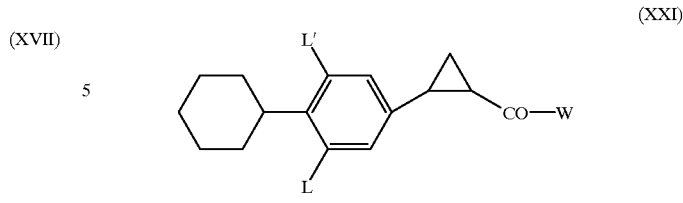
(XXI)

in which L and L' are as defined above and W is a hydroxyl group or a group of structure —$NG_1G_2$ where:

$G_1$ represents a $(C_1–C_6)$alkyl or a $(C_3–C_7)$cycloalkyl;

$G_2$ represents a $(C_1–C_6)$alkyl, a $(C_3–C_7)$cycloalkyl, a $(C_3–C_7)$cycloalkyl$(C_1–C_3)$alkyl; a phenyl, benzyl or phenethyl group optionally substituted with a halogen or with a methoxy or nitro group, or alternatively $G_1$ and $G_2$ form, together with the nitrogen atom to which they are attached, a saturated, bridged or spiro heterocycle having only one endocyclic nitrogen atom and containing from 5 to 10 carbon atoms; a morpholino group; a piperazino group which is unsubstituted or substituted in position 4 with a $(C_1–C_4)$alkyl, with a phenyl, benzyl or phenethyl radical, the phenyl nucleus optionally being substituted with a halogen or with a methoxy or nitro group; a group chosen from 4-phenyl-1,2,3,6-tetrahydropyrid-1-yl, 4-phenylpieridino, 4-benzyl-piperidino and 4-phenethylpiperidino radicals, it being possible for the phenyl groups of the said radicals to be unsubstituted or substituted with a halogen or with a methoxy group or a nitro group; as well as the alkali metal salts and secondary and tertiary amine salts and the functional derivatives of the acid of formula (XXI) where W is a hydroxyl group.

Among the alkali metal salts of the compounds of formula (XXI) where W is a hydroxyl group, the sodium salt (W=ONa) is particularly advantageous, whereas among the salts with secondary or tertiary amines, those of trimethylamine [W=O⁻, N⁻$(CH_3)_3$] and of triethylamine [W=O⁻, N⁻$(CH_2H_5)_3$] are particularly advantageous. Among the functional derivatives of the acid of formula (XXI) where W is Oh, the halides, in particular the chloride (W=Cl), the anhydride, the mixed anhydrides with a carboxylic or sulphonic acid, in particular those with carbonic acid mono $(C_1–C_4)$alkyl ester (W=O—COOAlk', Alk' being a $C_1–C_4$ alkyl, preferably ethyl), or with p-toluenesulphonic acid, and the activated esters, are particularly advantageous.

The compounds of formula (XXI) in which the halogen is preferably chloring or fluorine, one of the groups L and L' being hydrogen and the other fluorine, chlorine or nitro or alternatively L and L', which are identical, being hydrogen or chlorine, are particularly advantageous.

Among the latter compounds, those for which, in the formula (XXI), W is —OH, —ONa, O⁻, N⁺$(C_1H_5)_3$, Cl, O—COOAlk' (Alk' being $C_1–C_4$ alkyl) or —$NG_1G_2$ are preferred.

according to biochemical and pharmacological studies, exposure of the compounds used according to the invention to normal cells, under the same conditions as those which make it possible to obtain an antiproliferative activity on cancer cells, does not give rise to any detrimental effect on all the criteria examined, such as, for example, the integrity of the structures and of the cell functions or the maintenance of the viability. These products thus act with great specificity of action with request to tumour cells. The antitumour activity was established on several human tumour lines in vitro and in vivo in mice. The cells used were all obtained from the ATCC international collection. MCF-7 cells were used to perform the binding studies.

The membranes were prepared as follows: 10 MCF-7 cells are homogenized for 10 seconds on a Polytron® in 10 ml of Hepes® buffer pH=7.4 containing: 210 mM D-mannitol, 70 mM sucrose, 1 mM EDTA, 0.3 mM PMSF. The homogenate is centrifuged at 650 xg for 15 minutes and the supernatant is then taken up and centrifuged for 1 at 100,000 xg. The pellet is resuspended in Tris-HCl buffer pH=7.4 at a concentration of 1 mg/ml and stored at –70° C. The total binding is carried out in a 5 ml tube into which the following are introduced:

50 µl of membrane suspension containing 10 to 50 µg of proteins

175 µl of 50 mM Tris buffer pH=7.4

25 µl of 20 nM $^3$H SR 31747 in 50 mM Tris pH=7.4+0.1% BSA (bovine serum albumin).

The non-specific binding is performed by adding 25 µl of $10^{-5}$ M SR 31747 to the above solution (final volume 250 µl) and then incubating for 30 at 25° C. The free and bound fractions are separated by placing 200 µl on a column of 1 ml of Sephadex® LH 20 and the radioactivity is then counted on the first 2 ml obtained by eluting the column with 50 mM Tris buffer ph=7.4.

The compounds used according to the invention and the novel compounds showed $IC_{50}$ activities of between $10^{-10}$ and $10^{-6}$ M.

Among other cells used, the following lines were routinely cultured in RPMI medium supplemented with 10% foetal calf serum (FCS):

human myelomas U266 and RPMI 8226 human kidney carcinoma 294 human lung carcinoma A549 human mammary carcinoma MCF-7

MCF-7 human lymphocyte leukaemia

The antitumour activity is measured according to the colorimetry method using MTT, 3-(4,5-dimethylthiazole-2, 5-diphenyltetrazolium) bromide as described by Mosmann T., Journ. of Im. Methods; 1983, 65, 55.

This colorimetric assay makes it possible to measure quantitatively the antitumour activity of a solution containing a compound used according to the invention.

According to the procedure used, the suspended cells (such as the myeloma cells) are inoculated at $2\times10^3$ cells/ml in 1 ml wells in defined medium. The adherent cells (such as the MCF-7 cells) are inoculated at $5\times10^4$ cells/ml in 1 ml wells in RPMI medium+0.5% FCS overnight. The next day, the cell carpet is washed twice and replaced by the defined medium.

The defined medium corresponds to: RPMI+10 µg/ml insulin+10 µg/ml human transferrin.

In order to carry out this test, cells are maintained in the presence of the solution containing a compound used according to the invention for 5 days, and the MTT is then added to the culture medium.

The 5 day period which was selected corresponds to the optimum time for the activity. After culturing for 5 days, the proliferation of the cells is measured by the test described above. The optical density at 570 nm is measured. A blue coloration develops in the wells where the cells are still alive. The intensity of the coloration is proportional to the quantity of live cells.

The results obtained are described in Table A below.

TABLE A

Effect of SR 31747 on various human tumour lines after 5 days off treatment. The results are expressed as a percentage of cell proliferation relative to the untreated control taken as 100%

| ST 31747 | U266 | RPMI 8226 | MCF-7 | 293 | A549 |
|---|---|---|---|---|---|
| 10 µM | 11 | 6 | 5 | 7 | 10 |
| 1 µM | 52 | 9 | 34 | 10 | 14 |
| 100 nM | 67 | 54 | 58 | 36 | 38 |
| 10 nM | 82 | 66 | 75 | 43 | 50 |
| 1 nM | 95 | 79 | 83 | 80 | 56 |
| 100 pM | 100 | 91 | 100 | 84 | 88 |
| 10 pM | 100 | 100 | 100 | 100 | 100 |

It is seen that concentrations as low as 1 nM to 1 µM are sufficient to induce a 50% stoppage of the growth and that this effect is obtained on all the tumour cells examined.

The effect observed in vivo of inhibition of an MCF-7 cell line was studied in vivo in "nude" mice, intraperitoneally at doses of between 3 and 100 mg/kg in a model according to Neri C., et al.; Cancer Research, 1990, 50; 5892–5897 and according to Berebbi M., et al.; Oncogene, 1990, 5; 505–509.

Another study was also performed in order to determine the effect of SR 31747 on the in vitro and in vivo growth of mammary and prostate epithelial tumour cells.

The study consisted in evaluating the potential antitumour activity of SR 31747 on the growth of a variety of cancerous breast epithelial lines. The study is carried out in vitro on cell cultures, as well as in vivo after inoculation of tumoral mammary lines in "nude" athymic mice.

The cell lines which were used are as follows:

The hormone-sensitive MCF-7 line originates from a pleural effusion of a breast adenocarcinoma. The antioestrogen-resistant MCF-7LY2 cells were obtained from the MCF-7LCC1 and MCF-7LCC2 lines were developed in nude mice, after inoculation of the MCF-7 cells. The two lines are oestrogen-independent. The MCF-7CC2 cells are also antioestrogen-resistant. The MCF-7AZTD5 line is derived from the MCF-7 line after stable transfection with the H-ras oncogene. The MCF-7AZTD5 cells are antioestrogen-resistant in vitro. All of these lines are maintained on DMEM/F12 (1/1, vol/vol) containing 10% decomplemented foetal calf serum and 16 ng/ml of human insulin. The MCF-7LCC2 line is cultured in the permanent presence of $10^{-7}$ M hydroxytamoxifen. The MDA-MB231 tumoral mammary epithelial cells are oestrogen- and antioestrogen-insensitive. They are cultured in L15 medium supplemented with 10% FCS, 1% essential amino acids and 10 µg/ml of human insulin.

The InCaP, PC3 and DU145 epithelial lines are derived from prostate adenocarcinomas. Only the LnCaP cells are hormone-sensitive. The three lines are cultured in RPMI supplemented with 10% FCS.

All the lines are maintained at 37° C. in a humid air/$CO_2$ (95%/5%) atmosphere, except for the MDA-MB231 cells which are cultured in the absence of $CO_2$. THe cell lines are checked regularly free of mycoplasms.

The inoculation and treatment of the animals were carried out as follows:

The animals used are "nude" female athymic mice, which may or may not have been ovariectomized, obtained at 4 weeks old (R. Janvier). Before inoculating the hormone-sensitive mammary cells (MCF-7, MCF-7AZTD5), the animals receive 10 µl pf ethanolic $10^{-5}$ oestradiol solution applied percutaneously. The treatment is repeated three times over one week. One million cells suspended in 100 µl of PBS/Ca are inoculated subcutaneously above each of the hips. The following day, the animals receive 200 μl of injection solution (ethanol/Tween 80/physiological saline, 1/1/18, vol/vol) containing the various reactions at the predefined concentrations. The injections are made intraperitoneally and are repeated every day.

Results

In Vitro Activity of SR 31747 on the Proliferation of Various Tumoral Breast Epithelial Lines The results relating to the effect of SR 31747 on the proliferation of mammary epithelial cells in culture are given in Table B. The activity of SP 31747 was evaluated in the presence of various concentrations of saline. In the presence of reduced concentrations of saline, SR 31747 exerts an inhibitory action on the proliferation of all the tumor epithelial lines tested. Larger amounts of saline in the culture media partially or totally antagonize the inhibitory activity of SR 31747 on the cell growth.

For a given seral concentration, the capacity of SR 31747 to inhibit the proliferation also varies according to the line considered. In the presence of 0.1% FCS, which makes it possible both to maintain a minimum cell proliferation and to observe a consequent activity of SR 31747, the $IC_{50}$ determined for the hormone-sensitive MCF-7 lines (MCF-7, MCF-7AZ, MCF-7 22HTB) ranges from $2\times10^{-9}$ M to $7\times10^{-4}$ M. Similar $IC_{50}$ values are also obtained for the MDA-MB231 and MCF-7LCC cells. On the other hand, the MCF-7AZTD5 and MCF-7LY2 lines show greater sensitivities to the inhibitory action of SR 31747 since the $IC_{50}$ values determined are $2\times10^{-10}$ to $5\times10^{-}$M respectively.

In all cases, the virtually total inhibitions of the cell proliferation observed in the presence of $10^{-6}$ M and occasionally $10^{-7}$ M SR 31747 are, from all evidence, cytotoxic effects.

The results obtained also indicate that SR 31747 is incapable of reversing the stimulatory action of oestradiol on the hormone-sensitive MCF-7 line.

Table B—Effect of SR 31747 on the proliferation of mammary epithelial cells. Determination of the $IC_{50}$ after 6 days of treatment—medium changed every 48 hours In Vivo Effect of SR 31747 on the Frequency and Size of Tumours Developed After Inoculation of Tumoural Mammary Epithelial Lines in "Nude" Mice

Figure 1:
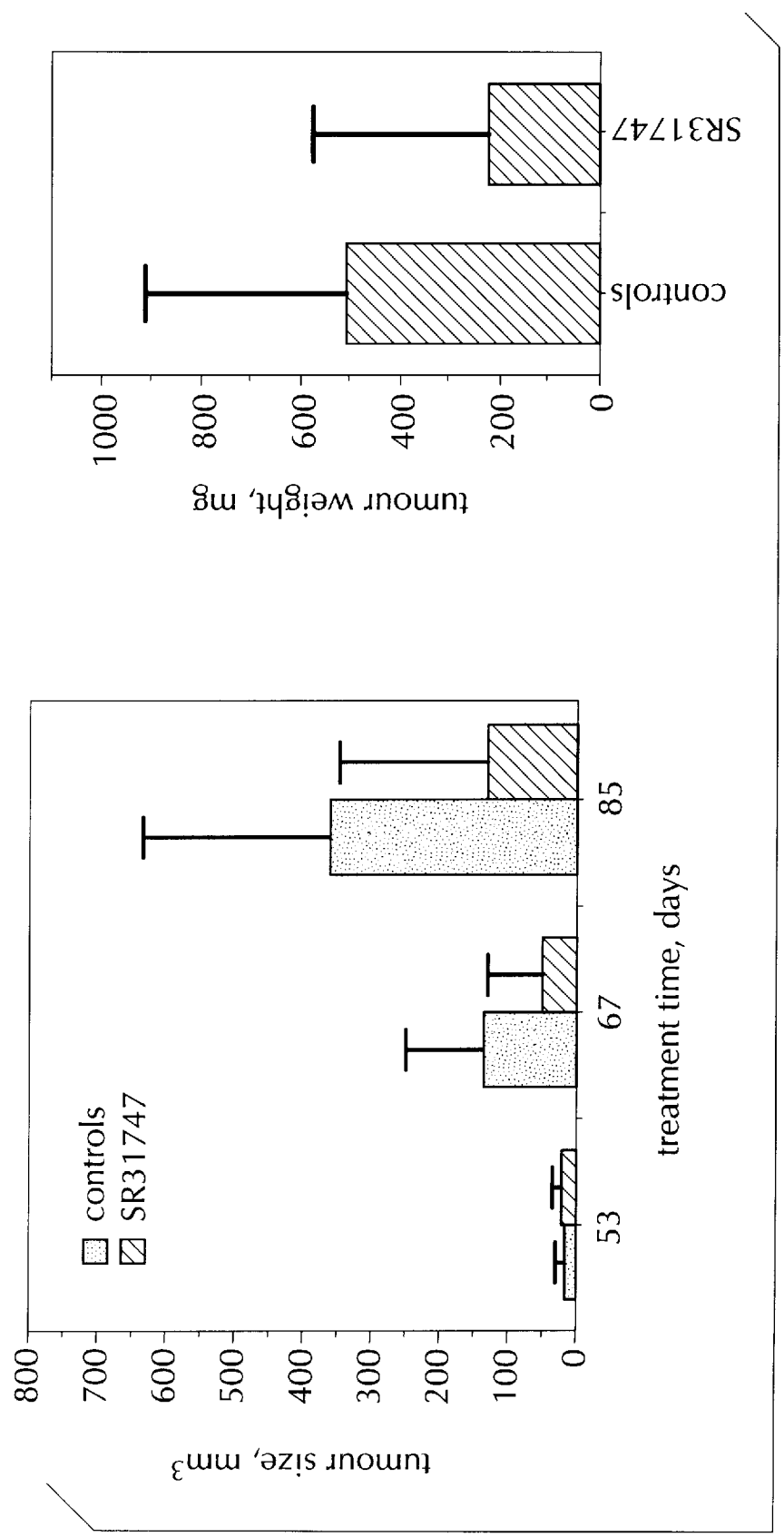
FIGS. 1 and 2 indicate the effect of SR 31747 on tumours developed in ovariectomized "nude" mice from MDA-MB231 cells.
Figure 2:
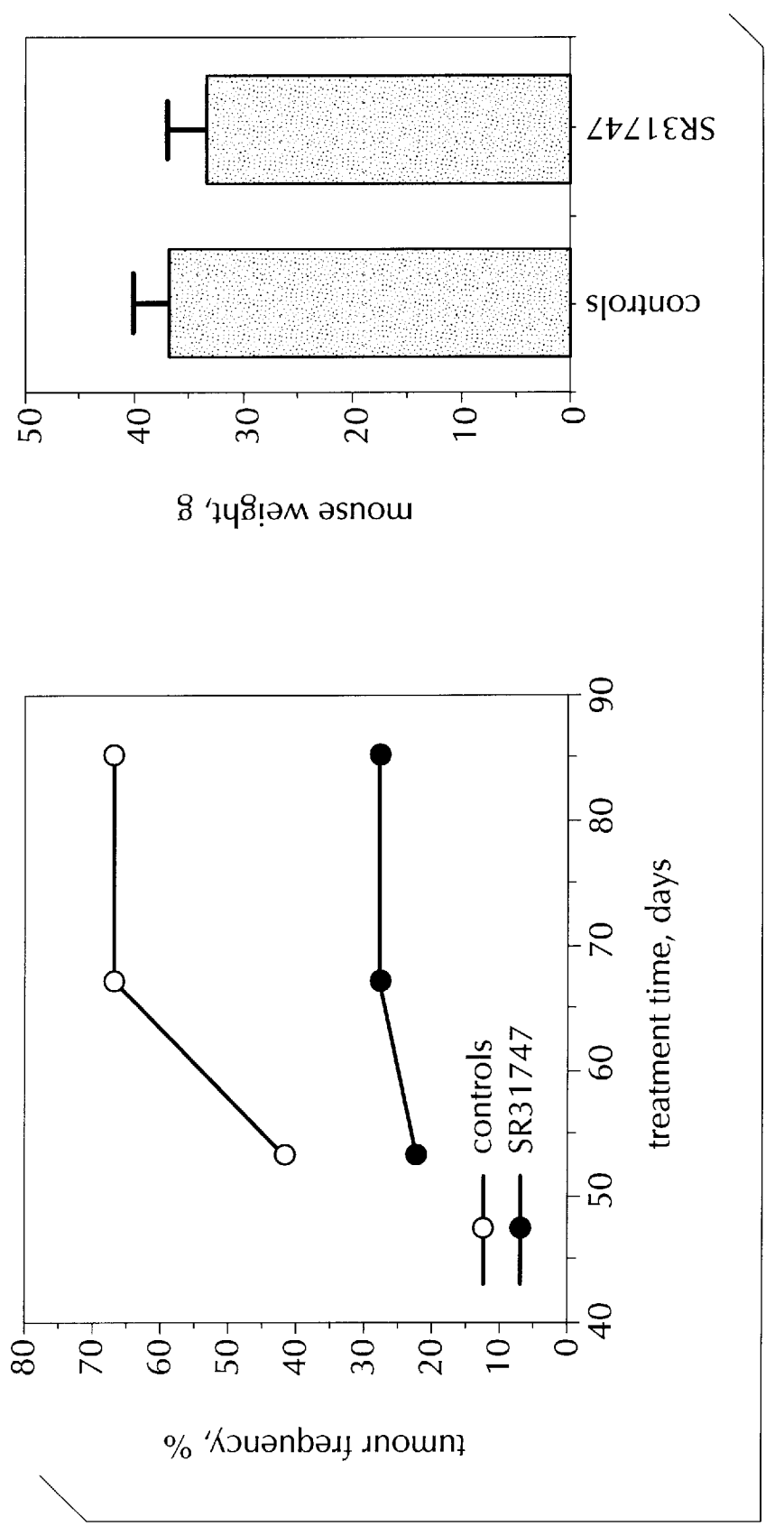

Each mouse receives $5\times10^6$ MDA-MB231 cells above each hip (i.e. 2 points of inoculation per mouse). The animals are then treated daily via the intraperitoneal route and receive 500 μg SR 31747+0.003 μg E2 (20 mice). The control batch receives 0.0003 μg E2 (20 mice). The amount (as a percentage of inoculated tumours) and size of the tumours developed are determined at different times in the course of the treatment. At the end of the treatment (day 92), the animals are sacrificed and weighed. The tumours are removed and weighed.

The figures show that SR 31747 has a tendency to reduce the size, weight and frequency of tumours developed in ovariectomized nude mice from MDA-MB231 cells. However, the differences in the size and weight of the tumours between control groups and SR 31747 do not appear to be significant, due to the large variability observed in each group.

Thus, in vitro SR 31747 do not appear to be significant, due to the large variability observed in each group.

Thus, in vitro SR 31747 has antiproliferative activity on the proliferation of all of the mammary tumoral epithelial cells studied. This activity is especially apparent in the presence of reduced concentrations of serum, and varies as a function of the lines considered. Although, in most cases, the IC50 values measured in 0.1% FCS vary between $2\times10^{-9}$ M and $2\times10^{-8}$ M, an extreme sensitivity of the MCF-7LY2 cells to SR 31747 is, however, observed.

A general tendency of SR 31747 to reduce, at the same time, the size, weight and frequency of tumours developed from MDA-MB231 cells is observed. The present invention

| Cells | Sensitivity | 10% FCS | 0.5% FCS | 0.1% FCS | 0% FCS |
|---|---|---|---|---|---|
| MCF7 p23-25 | hormone-sensitive | | $2 \times 5\ 10^{-7}$ M $10^{-7}$ M | $2 \times 10^{-9}$ M $2 \times 10^{-9}$ M | |
| MCF7 RPMI p6-7 | hormone-sensitive | | | $7 \times 10^{-9}$ M | $3 \times 10^{-9}$ M |
| MCF7 22HTB RPMI p + 4 | hormone-sensitive | | | $2 \times 10^{-9}$ M | |
| LY2 p22-23 | antioestrogen-resistant | $>10^{-7}$ M $>10^{-7}$ M | | $10^{-12}$ M $5 \times 10^{-12}$ M | |
| MCF7 AZTD5 | H-ras transfected antioestrogen | $6 \times 10^{-7}$ M | | $2 \times 10^{-10}$ M | |
| SN 47 p4 | normal cells | $>10^{-5}$ M | $4 \times 10^{-7}$ M | | |
| MCF7 AZ | hormone-sensitive | $>10^{-6}$ M | | $2 \times 5\ 10^{-7}$ M | |
| MCF7 + E2 10-9M | hormone-sensitive | | $4 \times 10^{-7}$ M $3 \times 10^{-7}$ M $4 \times 10^{-7}$ M | $5 \times 10^{-10}$ M $2 \times 10^{-9}$ M $2 \times 10^{-9}$ M | |
| MDA MB231 p131 | hormone-sensitive | $8 \times 10^{-7}$ M $4 \times 10^{-7}$ M | | $2 \times 10^{-9}$ M $2 \times 10^{-9}$ M | |
| LCC1 p23-24 | oestrogen-independent | 5% FCS $10^{-6}$ M | | $2 \times 10^{-9}$ M | |
| LCC2 p26-27 | oestrogen-independent antioestrogen-resistant | 5% DCC $4 \times 10^{-7}$ M $3 \times 10^{-7}$ M | | 0.1 DCC $2 \times 10^{-9}$ M $2 \times 10^{-9}$ M | | also relates to a technique of in vivo imaging of tumours which uses as target, for the compounds used according to the invention radiolabelled, for example, with $^{123}$I, $^{13}$F, $^{11}$C or $^{13}$N, the receptors to which the $^3$H SR 31747 binds. The reason for this is that the high density of these receptors in tumour cells has suggested that they may advantageously be used to bind the radioligands using the PET (positron emission tomography) and SPECT (single photon emission tomography) techniques.

The present invention thus relates also to the use of compounds radiolabelled with isotopes that are well known to those skilled in the art as imaging agents for radiolabelling.

Moreover, other imaging techniques involving an antigen-radiolabelled antibody complex may be used.

Such methods include, but are not limited to, the SPECT technique or the technique known as PET.

The use of the compounds according to the invention also comprises the preparation of medicinal products intended for therapy involving the targeting of radiolabelled products as radiation-releasing agents close to or in the tumour itself, using the said compounds to target radiolabelled products onto the tumour or its immediate environment in order to subject the tumour cells to the radiation emitted by the said radiolabelled products.

The use of the compounds according to the invention may also comprise a step of radiotherapy in which the cells in contact with the compounds undergo the effect of ionizing radiation including, for example, gamma-rays, beta-rays, X-rays or alpha particles which may be delivered by an external source as for the X-rays or gamma-rays, or by radionucleides which are administered directly to the patient as described, for example, in Principles of Radiation Therapy in Cancer, Principles and Practice of Oncology, Devita, V. T. et al. eds, 4th ed. J. B. Lippincott Co. Philadelphia, 1993, 15, 248–275.

These compounds may also be administered in combination with other anticancer active principles which are well known to those skilled in the art.

According to the biochemical and pharmacological studies illustrated above, the best activity was shown by the following compounds:

N-benzyl-N-methyl-[3-chloro-4-cyclohexylphenyl)-propyl]amine
1-(3-nitro-4-cyclohexylphenyl)-3-(4-phenylpiperidino)-propan-2-ol
trans-3-[3-(3nitro-4cyclohexylphenyl)allyl]-4-phenylpiperidine
1-[3-chloro-4-cyclohexylphenyl)prop-2-ynyl]-4-phenylpiperidine
1-[3-(3-chloro-4-cyclohexylphenyl)propyl]-4-phenyl-1,2,3,6-tetrahydropyridine
1-[3-(4-cyclohexylphenyl)propyl]-4-phenylpiperidine cis-3-[3-(3-chloro-4-cyclohexylphenyl)allyl]-3-aza-spiro[5.5]undecane
3-[3-(3-chloro-4-cyclohexylphenyl)propyl]-3-azaspiro[5.5]undecane
cis-N-adamantan-1-yl-N-ethyl[3-(3-chloro-4-cyclohexylphenyl)allyl]amine
4-benzyl-1-[3-(3-chloro-4-cyclohexylphenyl)propyl]-piperidine
1-(3-chloro-4-cyclohexylphenyl)-3-(4-phenylpiperidino)-propan-1-ol
N-cyclohexyl-N-ethyl[3-(4-cyclohexylphenyl)propyl]amine
cis-N-ethyl-N-phenyl[3-(3-chloro-4-cyclohexylphenyl)allyl]amine
N-benzyl-N-methyl[3-(3-chloro-4-cyclohexylphenyl)-propyl]amine
N-phenethyl-N-methyl-1-[3-(3-chloro-4-cyclohexyl-phenyl)propyl]amine
cis-N-cyclohexyl-N-ethyl-[3-(4-cyclohexylphenyl)allyl]-amine
N-cyclohexyl-N-ethyl[3-(3,5-dichloro-4-cyclohexyl-phenyl)allyl]amine
trans-N,N-dihexyl[3-(3-chloro-4-cyclohexylphenyl)-allyl]amine
cis-N-cyclohexyl-N-ethyl[3-(3-chloro-4-cyclohexyl-phenyl)allyl]amine
trans-N-cyclohexyl-N-ethyl[3-(3-chloro-4-cyclohexyl-phenyl)allyl]amine
N-cyclohexyl-N-ethyl[3-(3-chloro-4-cyclohexyl-phenyl)propyl]amine
1-[3-(3-chloro-4-cyclohexylphenyl)allyl]azepine trans-N,N-dicyclohexyl-3-[(3-chloro-4-cyclohexyl-phenyl)allyl]amine
N-cyclohexyl-N-ethyl[3-(3-chloro-4-cyclohexyl-phenyl)allyl]amine
N-cyclohexyl-N-ethyl[3-(3-chloro-4-cyclohexylphenyl)-prop-2-ynyl]amine
1-(3-chloro-4-cyclohexylphenyl)-3-(cyclohexyl-ethylamino)propan-1-one
1-(3-chloro-4-cyclohexylphenyl)-3-(cyclohexylethyl-amino)propan-1-ol
trans-M,M-diethyl-[3-(3-chloro-4-cyclohexylphenyl)-allyl]amine
4-[3-(3-chloro-4-cyclohexylphenyl)propyl]morpholine
4-[3-chlorohexylphenyl)but-2-enyl]morpholine
4-[4-(3-chloro-4-cyclohexylphenyl)butyl]morpholine
or one of their pharmaceutically acceptable salts or solvates.

The compounds capable of displacing $^3$H-SR 31747 from its receptors may be used in therapy in any pathological process which involves the proliferation of tumour cells. This cell proliferation may be either hormone-sensitive or hormone-insensitive.

More precisely, clinical applications for which the use of these compounds may be evisaged comprise diseases resulting from cell proliferation, in particular glioblastomas, neuroblastomas, lymphommas, myelomas, leukaemia and colon, colorectal, epithelial, hepatic, pulmonary, mammary, ovarian, pancreatic or prostate carcinomas.

For thses purposes, the compounds capable of displacing $^3$H-SR 31747 from its receptors, in particular the compounds of formulae (I) to (VIII) and their pharmaceutically acceptable salts, may be used for the preparation of oral, parenteral, sublingual, transdermal or topical pharmaceutical compositions. These pharmaceutical compositions contain at least one of the above products, in combination with a pharmaceutically inert vehicle.

More particularly, the present invention relates, according to another of its aspects, to pharmaceutical compositions containing, as active principle, a compound of formula (VIII) or one of its pharmaceutically acceptable salts.

Acids, both organic and inorganic, may be used to form addition salts with acids of the amines of formula (VIII) which are non-toxic and pharmaceutically acceptable, in particular sulphuric acid, nitric acid, phosphoric acid, hydrochloric acid, citric acid, acetic acid, lactic acid, tartaric acid, pamoic acid, ethanedisulphonic acid, methanesulphonic acid, succinic acid, cyclohexylsulphonic acid, fumaric acid, maleic acid and benzoic acid.

As regards oral or sublingual administration, simple or sugar-coated tablets, gelatine capsules, granules which may have a delayed-release action, drops or liposomes are used in particular. As regards intravenous, subcutaneous or intramuscular administration, use is made of sterile or sterilizable solutions, in particular for venous infusion, whereas conventional patches may be produced for transdermal administration. For topical use, creams or lotions to be spread on the skin may be used.

The pharmaceutical compositions according to the present invention may be prepared according to usual methods that are well known in the pharmaceutical technical field.

The active principle may be incorporated into the excipients usually used in the pharmaceutical compositions, such as talc, gum arabic, lactose, starch, magnesium stearate, aqueous or non-aqueous vehicles, fatty substances of animal or plant origin, paraffin derivatives, glycols, various wetting, dispersing or emulsifying agents, preserving agents, etc.

The pharmaceutical compositions of the invention may advantageously contain a compound of formula (VIII) or one of its pharmaceutically acceptable addition salts in combination with one or more other medicinal products known and commonly used for the same therapeutic indications.

The amount of active principle to be administered per day, according to the method of the present invention, depends on the specific nature of the therapeutic indication, the seriousness of the complaints to be treated and the weight of the patient and route of administration. For a systemic administration, the overall dose in man varies generally between 1 and 100 mg per day, for example from 2 to 50 mg and more appropriately from 3 to 40 mg per day.

Unit dosage forms for systemic administration will generally comprise from 3 to 50 mg (namely 3, 5, 10, 20, 30, 40 and 50 mg of product). These unit doses will normally be administered one or more times per day, preferably one to three times per day.

For topical administration, the pharmaceutical compositions generally contain from 0.0001 to 10% of active principles and preferably from 0.01 to 5%. The examples which follow illustrate the invention without, however, limiting it. In thses examples, Y means "yield" and m.p. means "melting point", determined on a Koffler heating block.

Preparation of the Acetylene Derivatives for the Production of the Cis Compounds Preparation 1

Semicarbazone Derivative

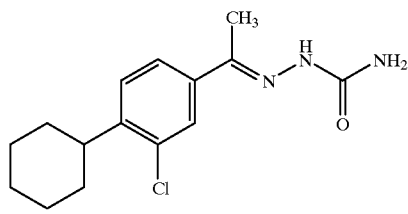

73.6 g (0.66 mol) of semicarbazide hydrochloride and 54.2 g (0.66 mol) of sodium acetate are dissolved in 600 ml of distilled water and the mixture is then stirred vigorously and 142.1 g (0.6 mol) of 3-chloro-4-cyclohexylacetophenone dissolved in 600 ml of ethanol are added rapidly at room temperature.

The reaction mixture is then heated at 50° C. for 2 hours and stirred at room temperature overnight, then the crystals formed are drained, washed with water, with acetone and with diethyl ether, dried and concentrated under vacuum in order to obtain 169.5 g of white crystals, Y=96%.

Preparation 2

2-Chloro-1-cyclohexyl-4-ethynylbenzene

The process is performed according to I. Lalezari et al., Agnew. Chem. Internat. ed., 1970, 9, 464.

A suspension of 26 g (0.234 mol) of finely ground selenium oxide and 58.7 g (0.2 mol) of semicarbazone obtained according to Preparation 1 in 400 ml of glacial acetic acid is first heated at 60° C. for 1 hour in an oil bath and then for 2 hours at 80° C., and the intermediate seleniodiazole is formed. The temperature of the oil bath is then raised to 150° C. and the reaction mixture is heated for three and a half hours, until the seleniodiazole has completely decomposed and the evolution of nitrogen has stopped. The acetic acid is then evaporated off under vacuum and the residue is, successively, taken up in 600 ml of diethyl ether, filtered, washed four times with water, once with aqueous 5% sodium hydroxide solution, twice more with water, dried over sodium sulphate and then evaporated under vacuum. The oil residue is distilled under $10^{-2}$ mm of mercury, temperature 85–100° C., to give 24.8 g of a colourless oil.

Preparation of the ketone derivatives by Mannich reaction in order to obtain the hydroxy precursors of the trans compounds Preparation 3

1-(3-Nitro-4-cyclohexylphenyl)-3-(4-phenylpiperidino)propanone 12.3 g of 3-nitro-4-cyclohexylacetophenone, 9.85 g of 4-phenylpiperidine, 7.5 g of paraformaldehyde and 1.5 ml of concentrated hydrochloric acid are dissolved in 100 ml of 1,2-dimethoxyethane and the reaction mixture is then heated at reflux with stirring for 6 hours. The reaction mixture is then left overnight at room temperature, after which a precipitate is separated out by filtration and washed successively with ethyl acetate and then with diethyl ether in order to give 17 g of the expected compound.

EXAMPLE 1

3-[3-(3-Chloro-4-cyclohexylphenyl)prop-2-ynyl]-3azaspiro[5.5]undecane hydrochloride 4.85 g (0.022 mol) of the compound obtained in Preparation 2 and 0.5 g of $CuCl_2$ are dissolved in 25 ml of 1,2-dimethoxyethane. A solution of 2.7 g of 35% formaldehyde and 3.74 g of 3-azaspiro[5.5]undecane in 20 ml of 1,2-dimethoxyethane is then added dropwise. After addition, the reaction mixture is heated at 70° C. for 30 minutes, the solvent is removed under vacuum and the residue is then, successively, taken up in diethyl ether, washed with aqueous 5% sodium hydroxide solution, with saturated sodium chloride solution and dried over magnesium sulphate. The hydrochloride is crystallized from ethyl acetate to give 7.6 g of the expected product; m.p.=241° C.

EXAMPLE 2 cis-3-[3-(3-Chloro-4-cyclohexylphenyl)allyl]-3-azaspiro[5.5]undecane hydrochloride 3 g of the hydrochloride of the acetylenic compound obtained in Example 1 above are liberated by aqueous 10% sodium hydroxide solution. The oil obtained after extraction with diethyl ether is washed with saturated sodium chloride solution, dried over magnesium sulphate and concentrated under vacuum. The residue thus obtained is taken up in 100 ml of ethyl acetate, 5 ml of methanol are added, followed by 0.2 g of Pd/BaSO$_4$ and the reaction mixture is hydrogenated at room temperature and at atmospheric pressure. The catalyst is separated out by filtration through silica, the filtrate is concentrated under vacuum and the residual oil is then chromatographed on a column of silica gel, eluent: 98/2 (v/v) dichloromethane/methanol. Concentration of the pure fractions gives the hydrochloride, which is recrystallized from ethyl acetate; Y=44%; m.p.=238° C.

EXAMPLES 3 AND 4

Working as described in Example 1, by reacting 4-cyclohexyl-3,5-dichloro-1-ethynylbenzene with, respectively, 4-phenylpiperidine and cyclohexylethylamine in the presence of formaldehyde, the following are respectively obtained:

4-phenyl-1-[3-(3,5-dichloro-4-cyclohexylphenyl)prop-2-ynyl]piperidine hydrochloride, m.p.=250° C. (Example 3);

N-cyclohexyl-N-ethyl-3-(3,5-dichloro-4-cyclohexylphenyl)prop-2-ynylamine hydrochloride (Example 4).

EXAMPLES 5 to 10

Workings as described in Example 1, by reacting 3-chloro-4-cyclohexyl-1-ethynylbenzene with, respectively, ethylphenylamine, 1-adamantylethylamine, benzylmethylamine, (2-phenylethyl)methylamine, 4-benzylpiperidine and 4-hydroxy-4-phenylpiperidine in the presence of formaldehyde, the following are respectively obtained:

N-ethyl-N-phenyl-3-(3-chloro-4-cyclohexylphenyl)prop-2-ynylamine hydrochloride (Example 5);

N-(1-adamantyl)-N-ethyl-3-(3-chloro-4-cyclohexylphenyl)prop-2-ynylamine hydrochloride (Example 6);

N-benzyl-N-methyl-3-(3-chloro-4-cyclohexylphenyl)prop-2-ynylamine hydrochloride (Example 7);

N-methyl-N-(2-phenylethyl)-3-(3-chloro-4-cyclohexylphenyl)prop-2-ynylamine hydrochloride (Example 8);

4-benzyl-1-[3-(3-chloro-4-cyclohexylphenyl)prop-2-ynyl]piperidine hydrochloride (Example 9); and 4-hydroxy-4-phenyl-1-[3-(3-chloro-4-cyclohexylphenyl)prop-2-ynyl]piperidine hydrochloride (Example 10).

EXAMPLES 11 AND 12

Working as described in Example 1, by reacting 4-cyclohexyl-1-ethynylbenzene with, respectively, cyclohexylethylamine and 4-phenylpiperidine in the presence of formaldehyde, the following are obtained:

N-cyclohexyl-N-ethyl-3-(4-cyclohexylphenyl)prop-2-ynylamine hydrochloride.

4-phenyl-1-[3-(4-cyclohexylphenyl)prop-2-ynyl]piperidine hydrochloride (Example 12).

EXAMPLES 13 TO 16

Working as described in Example 2, by hydrogenation of the acetylene derivatives obtained according to Examples 4 to 6 and 11, the cis-propenamines of Table I are obtained.

TABLE I cis compounds

| Example No. | L | L' | Z | m.p.; ° C. |
|---|---|---|---|---|
| 13 | Cl | Cl | | 189 HCl |
| 14 | Cl | H | | 124 HCl |
| 15 | Cl | H | | 234 HCl |
| 16 | H | H | | 184 HCl |

EXAMPLE 17

1-(3-Nitro-4-cyclohexylphenyl)-3-(4-phenylpiperidino)propanol 13.8 g of the ketone obtained in Preparation 3 are suspended in 300 ml of methanol. The mixture is cooled to −10° C., 8.42 g of sodium borohydride are then added and the reaction mixture is left at −10° C. for 10 minutes and is then allowed to warm to room temperature. The precipitate formed is separated out by filtration and washed with methanol to give 9.5 g of the expected product; m.p.= 148–150° C.

EXAMPLE 18 trans-1-[3-[3-(3-Nitro-4-cyclohexylphenyl)allyl]]-4-phenylpiperidine hydrochloride 10.6 g of the alcohol prepared in Example 17 and 10.4 g of para-toluenesulphonic acid are dissolved in 300 ml of xylene and the reaction mixture is then heated at reflux for 6 hours with stirring using Dean Stark apparatus to collect the water formed. The solvent is evaporated off under vacuum and the residual oil is then, successively, taken up in ethyl acetate, washed with aqueous 0.5N sodium hydroxide solution, dried over magnesium sulphate and concentrated under vacuum to 50 ml of solvent, into which hydrogen chloride gas is then bubbled. The mixture is concentrated under vacuum and the precipitate is rinsed with diethyl ether in order to obtain 8 g of the expected hydrochloride; m.p.=225–233° C.

EXAMPLE 19

3-(N-Ethyl-N-phenyl)amino-1-(3-chloro-4-cyclohexyl)phenylpropanol hydrochloride a) Working as described in Preparation 3, starting with 3-chloro-4-cyclohexylacetophenone, by reacting with phenylethylamine, 1-(3-chloro-4-cyclohexylphenyl)-3-(N-ethyl-N-phenylamino)propanone is obtained.

b) Working as described in Example 17, by reduction of the ketone obtained in step (a) with sodium borohydride, the expected product is obtained in the form of the hydrochloride; m.p.=219° C.

EXAMPLE 20

3-[3-(3-Chloro-4-cyclohexylphenyl)propyl]-3-azaspiro[5.5]undecane hydrochloride 3 g of the hydrochloride of the acetylene compound obtained in Example 1 are liberated with aqueous 10% sodium hydroxide solution. The oil obtained after extraction with diethyl ether is washed with saturated sodium chloride solution, dried over magnesium sulphate and concentrated under vacuum. The residual oil is then taken up in 100 ml of ethyl acetate, after which 5 ml of methanol are added, followed by 0.2 g of Pd/BaSO$_4$, and the reaction mixture is hydrogenated at room temperature and at atmospheric pressure. The catalyst is separated out by filtration through Celite and the filtrate is concentrated under vacuum. The residue obtained is taken up in the minimum amount of methanol in the presence of 50 ml of 2 N hydrochloric acid and is then successively extracted with dichloromethane, washed with 2N hydrochloric acid solution, with saturated sodium chloride solution, dried over magnesium sulphate and concentrated under vacuum in order to obtain 2 g of the expected hydrochloride; m.p.=266° C.

EXAMPLES 21 TO 26

Working as described in Example 20, by hydrogenation, respectively, of the acetylene derivatives prepared in Examples 11, 7, 8, 9, 12 and 10, the corresponding saturated derivatives of Table II are respectively obtained.

TABLE II

Structure: cyclohexyl-substituted phenyl ring with substituents L' (ortho), L (ortho), and Z (para).

| Example No. | L | L' | Z | m.p.; °C. |
|---|---|---|---|---|
| 21 | H | H | –CH$_2$CH$_2$CH$_2$–N(ethyl)(cyclohexyl) | 167 HCl |
| 22 | Cl | H | –CH$_2$CH$_2$CH$_2$–N(methyl)(benzyl) | 152 HCl |
| 23 | Cl | H | –CH$_2$CH$_2$CH$_2$–N(methyl)(phenethyl) | 166 HCl |
| 24 | Cl | H | –CH$_2$CH$_2$CH$_2$–(4-benzylpiperidin-1-yl) | 232–234 HCl |

TABLE II-continued

| Example No. | L | L' | Z | m.p.; °C. |
|---|---|---|---|---|
| 25 | H | H | (butyl-N-piperidinyl-phenyl) | 260 HCl |
| 26 | Cl | H | (butyl-N-(4-hydroxy-4-phenylpiperidinyl)) | 215 HCl |

EXAMPLE 27

1-[3-(3-Chloro-4-cyclohexylphenyl)propyl]-4-phenyl-1,2,3,6-tetrahydropyridine hydrochloride 1 g of the compound of Example 26 and 0.51 g of para-toluenesulphonic acid are dissolved in 25 ml of xylene. The reaction mixture is heated at reflux for 2 hours and then concentrated under vacuum. The residue is taken up in 10% sodium hydroxide solution and then, successively, extracted with dichloromethane, washed with water, with saturated sodium chloride solution, dried over magnesium sulphate and concentrated under vacuum in order to obtain 0.7 g of the expected hydrochloride; m.p.=210° C.

EXAMPLE 28 a) 4-(3-Chloro-4-cyclohexylphenyl)-4-hydroxybutyric acid.

20 g of 4-(3-chloro-4-cyclohexylphenyl)-4-oxobutyric acid are dissolved in 100 ml of tetrahydrofuran, 8.6 ml of aqueous sodium hydroxide solution and 100 ml of methanol are added. The reaction mixture is cooled to 0°–5° C. and 3.8 g of sodium borohydried are then added and the mixture is left overnight at room temperature.

This reaction mixture is poured into 8 l of water and 85 ml of concentrated hydrochloric acid are then added in order to obtain the expected hydroxy derivative.

b) 5-(3-Chloro-4-cyclohexylphenyl)dihydrofuran-2-one.

The compound obtained in (a) is dissolved in 300 ml of toluene and the reaction mixture is heated at reflux in the presence of Dean-Stark apparatus in order to remove the water. The solvent is then concentrated under vacuum in order to obtain the expected lactone; m=16 g; m.p.=60° C.

c) Methyl 4-chloro-4-(3-chloro-4-cyclohexylphenyl) butyrate.

2.78 g of lactone obtained in (b) are dissolved in 30 ml of benzene, 2.2 ml of thionyl chloride are then added dropwise and the reaction mixture is heated at reflux for 3 hours. This reaction mixture is then added to a cooled solution of hydrogen chloride gas in methanol and this mixture is stirred overnight at room temperature and then concentrated under vacuum in order to obtain 3.5 g of the expected chloro derivative.

d) 2-(3-Chloro-4-cyclohexylphenyl) cyclopropanecarboxylic acid.

3 g of the ester obtained in (c) are dissolved in 10 ml of t-butanol, 1.5 g of potassium tert-butoxide are then added and this mixture is heated at reflux for 4 hours. After cooling, 50 ml of water are then added and the mixture is extracted with diethyl ether. After concentration of the solvent, saponification is then carried out by dissolving the residue in 20 ml of ethanol and 10 ml of water in the presence of 0.8 g of potassium hydroxide, and this reaction mixture is then heated at reflux for 2 hours. After cooling the solution, water is added, the mixture is acidified by addition of 6N hydrochloric acid and is extracted with diethyl ether, dried and concentrated under vacuum in order to obtain 1.4 g of the expected acid.

EXAMPLES 29 TO 32 a) Working as described in Example 28 (a), starting with 4-(4-cyclohexylphenyl)-4-oxobutyric acid, 4-(4-cyclohexyl-3,5-dichlorophenyl)-4-oxobutyric acid, 4-(4-cyclohexyl-3-fluorophenyl)-4-oxobutyric acid and, respectively, 4-(4-cyclohexyl-3-nitrophenyl)-4-oxobutyric acid, by reduction with sodium borohydride, the following are obtained:

4-(4-cyclohexylphenyl)-4-hydroxybutyric acid (Example 29a);

4-(4-cyclohexyl-3,5-dichlorophenyl)-4-hydroxybutyric acid (Example 30a);

4-(4-cyclohexyl-3-fluorophenyl)-4-hydroxybutyric acid (Example 31a); and, respectively, 4-(4-cyclohexyl-3-nitrophenyl)-4-hydroxybutyric acid (Example 32a)

b) Working as described in Example 28 (b), starting with the hydroxybutyric acids obtained in Examples 29a to 32a above, by heating or reflux in toluene in the presence of Dean-Stark apparatus, the following are obtained:

5-(4-cyclohexylphenyl)dihydrofuran-2-one (Example 29b)

5-(4-cyclohexyl-3,5-dichlorophenyl)dihydrofuran-2-one (Example 30b)

5-(4-cyclohexyl-3-fluorophenyl)dihydrofuran-2-one (Example 31b) and, respectively, 5-(4-cyclohexyl-3-nitrophenyl)dihydrofuran-2-one (Example 32b)

c) Working as described in Example 28 (c), by reaction of the lactones obtained in Examples 29 (b) and 32 (b) above with thionyl chloride and then with HCl in methanol, the following are obtained:

methyl 4-chloro-4-(4-cyclohexylphenyl)butyrate (Example 29c);

methyl 4-chloro-4-(4-cyclohexyl-3,5-dichlorophenyl) butyrate (Example 30c);

methyl 4-chloro-4-(4-cyclohexyl-3-fluorophenyl)butyrate (Example 31c); and, respectively, methyl 4-chloro-4-(4-cyclohexyl-3-nitrophenyl)butyrate (Example 31d).

d) Working as described in Example 28 (d), by heating the esters obtained in Examples 29 (c) to 32 (c) above in t-butanol in the presence of potassium t-butoxide, the following are obtained:

2-(4-cyclohexylphenyl)cyclopropanecarboxylic acid (Example 29d);

2-(4-cyclohexyl-3,5-dichlorophenyl)cyclopropanecarboxylic acid (Example 30d);

2-(4-cyclohexyl-3-fluorophenyl)cyclopropanecarboxylic acid (Example 31d) and, respectively, 2-(4-cyclohexyl-3-nitrophenyl)cyclopropanecarboxylic acid (Example 32d).

EXAMPLE 33 a) 2-(3-Chloro-4-cyclohexylphenyl)cyclopropanecarboxylic acid chloride.

4 g of the acid obtained in Example 28 and 3.7 ml of thionyl chloride are dissolved in 50 ml of carbon tetrachloride. The reaction mixture is heated at reflux for 3 hours and is then concentrated under vacuum in order to obtain 5.9 g of the expected acid chloride in the form of an oil.

b) N-cyclohexyl-N-ethyl-2-(3-chloro-4-cyclohexylphenyl)cyclopropanecarboxamide.

3 g of acid chloride prepared above are dissolved in 50 ml of carbon tetrachloride, 2.9 g of cyclohexylethylamine dissolved in 50 ml of carbon tetrachloride are then added and the reaction mixture is stirred at room temperature for 20 hours. The solution is then washed with water to neutral pH in order to obtain 5.16 g of amide in the form of an oil.

EXAMPLES 34 TO 37 a) Starting with the cyclopropanecarboxylic acids obtained as indicated in Examples 29 (d) to 32 (d), but reaction with thionyl chloride as described in Example 33 (a), the following are obtained:

2-(4-cyclohexylphenyl)cyclopropanecarboxylic acid chloride (Example 34a);

2-(4-cyclohexyl-3,5-dichlorophenyl)cyclopropanecarboxylic acid chloride (Example 35a);

2-(4-cyclohexy-3-fluorophenyl)cyclopropanecarboxylic acid chloride (Example 36a) and, respectively, 2-(4-cyclohexyl-3-nitrophenyl)cyclopropanecarboxylic acid chloride (Example 37a).

b) Working as described in Example 33 (b), by reaction of the acid chlorides obtained in Examples 34 (a) to 37 (a) above with cyclohexylethylamine, the following are obtained:

N-cyclohexyl-N-ethyl-2-(4-cyclohexylphenyl)cyclopropanecarboxamide (Example 34b)

N-cyclohexyl-N-ethyl-2-(4-cyclohexyl-3,5-dichlorophenyl)cyclopropanecarboxamide (Example 35b)

N-cyclohexyl-N-ethyl-2-(4-cyclohexyl-3-fluorophenyl) cyclopropanecarboxamide (Example 36b)

N-cyclohexyl-N-ethyl-2-(4-cyclohexyl-3-nitrophenyl) cyclopropanecarboxamide (Example 37b)

EXAMPLE 38

[2-(3-Chloro-4-cyclohexylphenyl) cyclopropylmethyl]cyclohexylethylamine hydrochloride 5.1 g of the amide obtained in Example 33 are dissolved in 50 ml of diethyl ether, a suspension of 0.99 g of lithium aluminum hydride in diethyl ether is then added and the reaction mixture is stirred for 3 hours at room temperature and then poured into aqueous 5% sodium hydroxide solution. The reaction mixture is then extracted with ether and then, successively, the organic phase is separated out by settling, dried over magnesium sulphate and hydrogen chloride gas is bubbled through the solution in order to obtain 3.54 g of the expected hydrochloride; m.p.=202° C.

EXAMPLE 39 a) Working as described in Preparation 3, starting with 3-chloro-4-cyclohexylacetophenone, by reaction with di-n-hexylamine and formaldehyde, 1-(3-chloro-4-cyclohexylphenyl)-3-dihexylaminopropanone is obtained.

b) Working as described in Example 17, by reduction of the ketone obtained in step (a) with sodium borohydride, 3-dihexylamino-1(3-chloro-4-cyclohexylphenyl)propanol is obtained.

c) Working as described in Example 18, by dehydration of the alcohol obtained in step (b), N-trans-[3-(3-chloro-4-cyclohexylphenyl)allyl]dihexylamine is obtained; m.p.=128° C.

EXAMPLES 40 TO 52

Starting with 2-(3-chloro-4-cyclohexylphenyl)cyclopropanecarboxylic acid chloride, obtained as described in Example 33 (a), by reaction, respectively, with diethylamine, dihexylamine, (1-adamantyl)ethylamine, ethylphenylamine, benzylmethylamine, methyl(2-phenylethyl)amine, morpholine, piperidine, 4-phenyl-1,2,3,6-tetrahydropyridine, 4-phenylpiperidine, 4-benzylpiperidine, 4-(2-phenylethyl)piperidine, 3-azaspiro[5.5]undecane, and working according to the indications of Example 33 (b), the following are obtained:

N,N-diethyl-2-(3-chloro-4-cyclohexylphenyl)cyclopropanecarboxamide (Example 40);

N,N-dihexyl-2-(3-chloro-4-cyclohexylphenyl)cyclopropanecarboxamide (Example 41);

N-(1-adamantyl)-N-ethyl-2-(3-chloro-4-cyclohexylphenyl)cyclopropanecarboxamide (Example 42);

N-ethyl-N-phenyl-2-(3-chloro-4-cyclohexylphenyl)cyclopropanecarboxamide (Example 43);

N-benzyl-N-methyl-2-(3-chloro-4-cyclohexylphenyl)cyclopropanecarboxamide (Example 44);

N-methyl-N-(2-phenylethyl)-2-(3-chloro-4-cyclohexylphenyl)cyclopropanecarboxamide (Example 45);

4-[2-(3-chloro-4-cyclohexylphenyl)cyclopropyl]carbonylmorpholine (Example 46);

1-[2-(3-chloro-4-cyclohexylphenyl)cyclopropyl]
carbonylpiperidine (Example 47);

1-[2-(3-chloro-4-cyclohexylphenyl)cyclopropyl]
carbonyl-4-phenyl-1,2,3,6-tetrahydropyridine
(Example 48);

1-[2-(3-chloro-4-cyclohexylphenyl)cyclopropyl]
carbonyl-4-phenylpiperidine (Example 49);

1-[2-(3-chloro-4-cyclohexylphenyl)cyclopropyl]
carbonyl-4-benzylpiperidine (Example 50);

1-[2-(3-chloro-4-cyclohexylphenyl)cyclopropyl]
carbonyl-4-(2-phenylethyl)piperidine (Example 51);

3-[2-(3-chloro-4-cyclohexylphenyl)cyclopropyl]
carbonyl-3-azaspiro[5.5]undecane (Example 52);

EXAMPLES 53 TO 65

Working as described in Example 38, by reduction of the amides obtained in Examples 40 to 52, the following are obtained:

N,N-diethyl-2-(3-chloro-4-cyclohexylphenyl)
cyclopropylmethanamine (Example 53);

N,N-dihexyl-2-(3-chloro-4-cyclohexylphenyl)
cyclopropylmethanamine (Example 54);

N-(1-adamantyl)-N-ethyl-2-(3-chloro-4-
cyclohexylphenyl)cyclopropylmethanamine (Example 55);

N-ethyl-N-phenyl-2-(3-chloro-4-cyclohexylphenyl)
cyclopropylmethanamine (Example 56);

N-benzyl-N-methyl-2-(3-chloro-4-cyclohexylphenyl)
cyclopropylmethanamine (Example 57);

N-methyl-N-(2-phenylethyl)-2-(3-chloro-4-
cyclohexylphenyl)cyclopropylmethanamine (Example 58);

4-[2-(3-chloro-4-cyclohexylphenyl)cyclopropyl]
methylmorpholine (Example 59);

1-[2-(3-chloro-4-cyclohexylphenyl)cyclopropyl]
methylpiperidine (Example 60);

1-[2-(3-chloro-4-cyclohexylphenyl)cyclopropyl]methyl-
4-phenyl-1,2,3,6-tetrahydropyridine (Example 61);

1-[2-(3-chloro-4-cyclohexylphenyl)cyclopropyl]methyl-
4-phenylpiperidine (Example 62);

1-[2-(3-chloro-4-cyclohexylphenyl)cyclopropyl]methyl-
4-benzylpiperidine (Example 63);

1-[2-(3-chloro-4-cyclohexylphenyl)cyclopropyl]methyl-
4-(2-phenylethyl)piperidine (Example 64);

3-[2-(3-chloro-4-cyclohexylphenyl)cyclopropyl]methyl-
3-azaspiro[5.5]undecane (Example 65);

EXAMPLE 66

N-Cyclohexyl-N-ethyl-2-(3-chloro-4-
cyclohexylphenyl)cyclopropanecarboxamide a) 1.34 g (12.3 mmol) of ethyl chloroformate are added to a solution of 3.4 g (12.2 mmol) of 2-(3-chloro-4-cyclohexylphenyl)cyclopropanecarboxylic acid and 1.25 g (12.3 mmol) of triethylamine in 50 ml of dioxane, cooled to −5° C. This internal temperature is maintained for 20 minutes with stirring, the mixture is then allowed to warm to room temperature, the triethylamine hydrochloride is filtered off and the solution of the mixed anhydride of 2-(3-chloro-4-cyclohexylphenyl)cyclopropanecarboxylic acid and of monoethyl ester of the carbonic acid thus obtained is used.

A solution of 1.56 g of cyclohexylethylamine in 30 ml of tetrahydrofuran is added to the solution of the mixed anhydride thus obtained and the reaction mixture is stirred or 8 hours at room temperature. The solution is then washed with water and dried and the solvent is evaporated off. N-Cyclohexyl-N-ethyl-2-(3-chloro-4-cyclohexylphenyl)cyclopropanecarboxamide is thus obtained.

What is claimed is:

1. A method of combating tumor or cancer cell proliferation which comprises administering to a patient in need of such treatment an effective amount of cis-N-cyclohexyl-N-ethyl[3-(3-chloro-4-cyclohexylphenyl)allyl]amine or a pharmaceutically acceptable salt or solvate thereof.

2. A method according to claim 1, wherein the cell proliferation is hormone-sensitive.

3. A method according to claim 1, wherein the cell proliferation is hormone-insensitive.

* * * * *

UNITED STATES PATENT AND TRADEMARK OFFICE
CERTIFICATE OF CORRECTION

PATENT NO. : 6,235,791 B1  Page 1 of 2
DATED : May 22, 2001
INVENTOR(S) : Breliere et al.

It is certified that error appears in the above-identified patent and that said Letters Patent is hereby corrected as shown below:

Column 14,
Line 59, "according" should read as -- According --

Column 15,
Line 23, after "30" add the word -- minutes --
Line 27, "ph=7.4" should read as -- pH=7.4 --

Column 16,
Line 37, after "the" insert the following: MCF-7 line by selective pressure in the presence of a high-affinity antioestrogen. The --
Line 39, "MCF-7CC2" should read as -- MCF-7LCC2 --

Column 17,
Line 3, "reactions" should read as -- reactants --
Line 11, "SP 31747" should read as -- SR 31747 --

Column 18,
Lines 26-27 should be deleted as this is duplicate language to what already appears in column 18, lines 24-25 and 28

Column 20,
Line 42, "lymphommas" should read as -- lymphomas --
Line 45, "thse" should read as -- these --
Line 66, "gelatine" should read as -- gelatin --

UNITED STATES PATENT AND TRADEMARK OFFICE
CERTIFICATE OF CORRECTION

PATENT NO. : 6,235,791 B1
DATED : May 22, 2001
INVENTOR(S) : Breliere et al.

It is certified that error appears in the above-identified patent and that said Letters Patent is hereby corrected as shown below:

<u>Column 21,</u>
Lines 37-38, "principles" should read as -- principle --
Line 40, "thse" should read as -- these --

Signed and Sealed this

Twenty-eighth Day of May, 2002

*Attest:*

*Attesting Officer*

JAMES E. ROGAN
*Director of the United States Patent and Trademark Office*